United States Patent [19]

Koch et al.

[11] Patent Number: 5,646,177

[45] Date of Patent: Jul. 8, 1997

[54] GLUTATHIONE DERIVATIVES OF ANTHRACYCLINES

[75] Inventors: Tad H. Koch; Giorgio Gaudiano, both of Boulder, Colo.

[73] Assignees: Board of Regents of The University of Colorado, Boulder, Colo.; Consiglio Nazionale Delle Richerche, Rome, Italy

[21] Appl. No.: 432,836

[22] Filed: May 2, 1995

[30] Foreign Application Priority Data

May 2, 1994 [IT] Italy .................... RM94A0269

[51] Int. Cl.⁶ .................... C07D 319/04; C07D 319/08; C07D 50/22
[52] U.S. Cl. .................... 514/452; 514/562; 549/358; 552/201; 562/427
[58] Field of Search .................... 562/427; 514/562, 514/452; 549/358; 552/201

[56] References Cited

PUBLICATIONS

Gaudiano, G. et al. (1994) *J. Amer. Chem. Soc.* 116:6537–6544.
Houee–Levin, C. et al. (1991) *Free Rad. in Biol. Med.* 11:573–580.
Vance, R.B. et al. (1991) *Investigation New Drugs* 9:73–75.
Tewey, K.M. et al. (1984) *Science* 226:466–468.
Bachur, N.R. et al. (1979) *Proc. Natl. Acad. Sci. USA* 76:954–957.
Moore, H.W. and Czerniak, R. (1981) *Med. Res. Rev.* 1:249–280.
Lin, T–S. et al. (1984) *J. Med. Chem.* 27:813–815.
Abdella et al. (1985) *Environ. Health Perspect.* 64:3–18.
Thompson, D.C. et al. (1992) *Chem.–Biol. Interact.* 86:129–162.
Tritton, T. (1991) *Pharmacol. Ther.* 49:293–309.
Myers, C.E. et al. (1977) *Science* 197:165–167.
Doroshow, J.H. et al. (1986) *J. Biol. Chem.* 261:3068–3074.
Volm, M. et al. (1991) *Br. J. Cancer* 64:700–704.
Giai, M. et al. (1991) *Eur. J. Cynecol. Oncol.* 12:359–373.
Black, S.M. and Wolf, C.R. (1991) *Pharmacol. Ther.* 51:139–154.
Anders, M.W. et al. (1992) *Xenobiotica* 22:1135–1145.
Olson, J.A. et al. (1992) *J. Nutr.* 122 (3rd suppl.):615–624.
Waxman, D.J. (1990) *Cancer Res.* 50:6449–6454.
Baillie, T.A. et al. (1991) *Acc. Chem. Res.* 24:264–270.
Tsuchida, S. et al. (1992) *Rev. Biochem. Mol. Biol.* 27:337–384.
Schecter, R.L. et al. (1992) *Biochem. Cell Biol.* 70:349–353.
Meijer, C. et al. (1991) *Int. J. Cancer* 49:582–586.
Peters, W.H. and Roelofs, H.M.J. (1992) *Cancer Res.* 52:1886–1890.

*Primary Examiner*—Johann Richter
*Assistant Examiner*—Laura L. Stockton
*Attorney, Agent, or Firm*—Greenlee, Winner and Sullivan, P.C.

[57] ABSTRACT

Disclosed herein are new anthracyclines which are derived from conjugation with glutathione, for example from conjugation of adriamycin, daunomycin and menogaril with glutathione: compounds 7 I, 7 II, 8 I, 8 II, 9 I and 9II, are obtained by reduction of the anthracycline followed by reaction of the reduced product with glutathione in aqueous ($H_2O$ or $D_2O$) or organic solvent. The invention also provides salts of these glutathione derivatives, particularly salts formed from anthracycline glutathione anions with anthracycline cations. These anthracycline derivatives are useful as antibiotics, as antitumor agents, and in the treatment of AIDS. These derivatives are particularly useful in the treatment of cancer when multiple drug resistance is present.

11 Claims, No Drawings

GLUTATHIONE DERIVATIVES OF ANTHRACYCLINES

This invention was made at least in part under grants from the U.S. Government through the National Science Foundation and the National Cancer Institute. The United States government has certain rights in this invention.

BACKGROUND OF THE INVENTION

Anthracyclines are among the most active antitumor agents. They are important in the treatment of leukemia and solid tumors. Among anthracyclines, adriamycin (doxorubicin) (1) is a broad spectrum antitumor drug of significant clinical utility. Arcamone, F. (1981) *Doxorubicin Anticancer Antibiotics*, Academic Press, New York. Daunomycin (daunorubicin) (2) is also used widely to treat leukemia. Menogaril (3), a semisynthetic anthracycline, whose structure is quite different from (1) and (2), is an antitumor drug in phase II of clinical trials. Vance, R. B. et al. (1991) Investigation New Drugs 9:73.

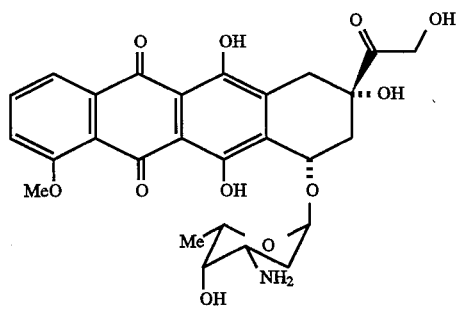

R = OH, adriamycin (1)
R = H, daunomycin (2)

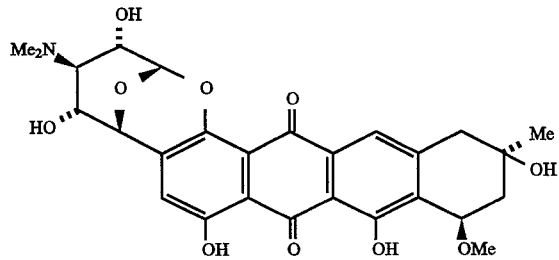

menogaril (3)

Anthracyclines are believed to exert their antitumor activity and their cytotoxicity because they are able to intercalate in and cleave DNA, and/or catalysis of superoxide formation, and/or they can be bioreduced to the corresponding quinone methides (Q.M., e.g., 4) that can function as alkylating agents, and catalysts for oxygen reduction, leading to highly toxic radicals. Tewey, KM et al. Science (1984) 226:466; Bachur, NR et al. Proc. Natl. Acad. Sci. USA (1979) 76:954; Gaudiano, G; Koch, T, Chem. Res. in Toxicology (1991) 4:2; Moore, HW, Czerniak, R Med. Res. Rev. (1981) 1:249; Lin, T-S et al. *J. Med. Chem.* (1984) 111:2283; Abdella, BRJ, Fisher, J Environ. Health Perspect. (1985) 64:3; Thompson, DC et al. Chem.-Biol. Interact. (1992) 86:129. The intercalation process appears to be augmented through anthracycline interaction with the cell membrane. Tritton, T, Pharmacol. Ther. (1991) 49:293. The formation of superoxide is thought to result in oxidative stress which in the myocardium is a possible source of cardiotoxicity. Myers, CE et al. Science (1977) 197:165; Doroshow, JH et al. *J. Biol. Chem* (1986) 261:3068.

Multidrug resistance can be induced upon administration of anthracyclines, particularly adriamycin. Multidrug resistance is characterized by resistance to several drugs developed by a variety of tumor cells upon treatment with adriamycin or other single drugs. Mechanisms proposed for tumor cell multidrug resistance include over expression of P-170-glycoprotein or other proteins, resulting in enhanced efflux of the drug and increased glutathione concentration and over expression of glutathione transferase. Volm, M et al. *Br. J. Cancer* (1991) 64:700; Giai, M et al. Eur. J. Gynecol. Oncol. (1991) 12:359; Black SM, Wolf, CR Pharmacol. Ther. (1991) 51:139.

Glutathione transferase catalyzes the formation of drug-glutathione conjugates which commonly, but not always, have lower cytotoxicity and/or may be expelled from the cell. Anders, MW et al. Xenobiotics (1992) 22:1135; Olson, JA et al. *J. Nutr.* (1992) 122(3rd Suppl.):615; Waxman, DJ Cancer Res. (1990) 50: 6449; Baillie, TA et al. Acc. Chem. Res. (1991) 24:264; Tsuchida, S. et al. Rev. Biochem. Mol. Biol. (1992) 27:337; Schecter, RL et al. *Biochem Cell Biol.* (1992) 70:439. A significant increase in glutathione concentration and glutathione transferase activity has been reported in adriamycin insensitive cells relative to sensitive cells. Meijer, C et al. *Int. J. Cancer* (1991) 49:582; Peters, WH, Roelofs, HMJ Cancer Res. (1992) 52:1886.

The synthesis of a number of anthracyclines carrying a variety of different substituents at the position C-7 has been reported. Some of these derivatives have been used as antitumor drugs. It is also known that in the anthracyclines used as antitumorals, the residue at position C-7 is usually polar in nature. No successful synthesis of anthracycline derivatives with C-7 peptide residues has been reported. Houee-Levin, C. et al. (1991) Free Rad. in Biol. Med. 11:573) reported a failed attempt to synthesize the glutathione derivative of daunomycin.

SUMMARY OF THE INVENTION

The present invention relates to novel derivatives of anthracyclines and semi-synthetic anthracyclines which are substituted at the C-7 position with glutathione, GSH (5), moiety. GSH is a sulfur-containing natural tripeptide. These derivatives are glutathione-aglycon conjugates of anthracyclines.

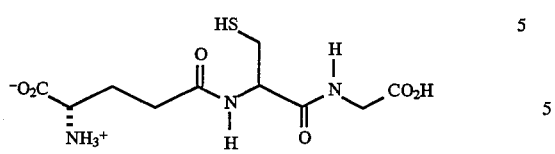

More specifically, the invention relates to glutathione derivatives of adriamycin (7), daunomycin (8) and menogaril (9):

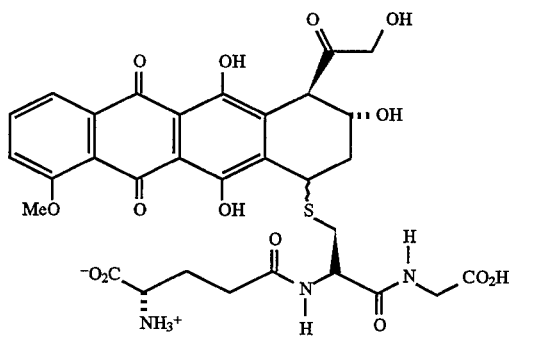

7-S-glutathionyl-7-deoxyadriamycinone
7I and 7II

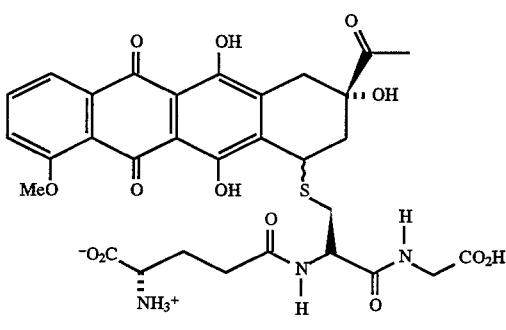

7-S-glutathionyl-7-deoxydaunomycinone
8I and 8II

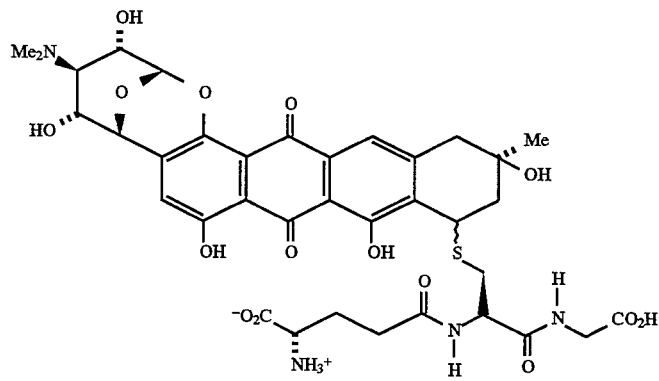

In each case both stereoisomeric (at C-7) glutathione derivatives (I and II) have been synthesized. The 7-S-glutathionyl derivatives of adriamycin, daunomycin and menogaril are referred to herein as ADRIGLU (I and II), DAUNOGLU (I and II) and MENOGLU (I and II), respectively, where I and II refer to the two different stereoisomers at C-7.

This invention also provides pharmaceutically acceptable salts of the glutathione derivatives of anthracyclines and semi-synthetic anthracyclines.

This invention further provides salts of the glutathione derivatives of anthracyclines in which an anthracycline is the conjugate cation as for example 13, the salt of adriamycin cation with the glutathionyl adriamycin conjugate anion (ADRIGLU salt):

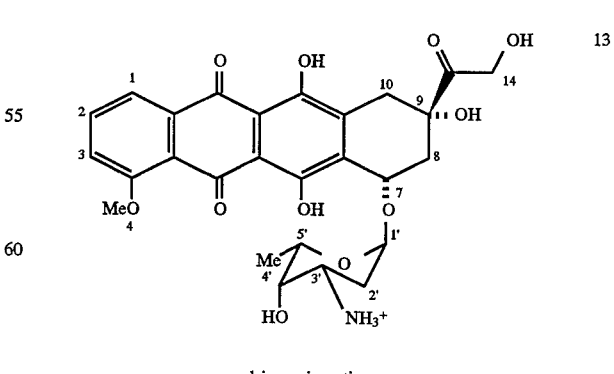

adriamycin cation

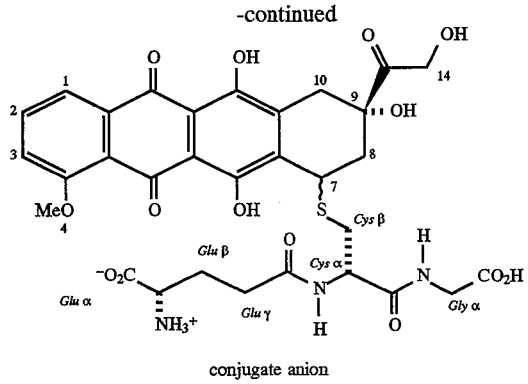

conjugate anion

Salts of anthracycline cations with the analogous glutathionyl anthracycline conjugate anion are also provided, including the DAUNOGLU salt and the MENOGLU salt. Mixed salts in which the cation of one anthracycline is combined with the glutathionyl conjugate anion of another anthracycline are also provided.

These new anthracycline derivatives and salts are useful alone or in combination with each other as antibiotic, anti-tumor and anti-cancer agents. These derivatives and salts are particularly useful in cases where multidrug resistance occurs.

The invention also relates to pharmaceutical and therapeutic compositions which contain a pharmaceutically or therapeutically effective amount of these derivatives and salts and to therapeutic methods and methods of treatment employing such compositions. In particular, this invention relates to methods of treating cancer including leukemia and soft-tissue cancers by administration of the glutathionyl anthracycline derivatives and their salts. A method of treatment of cancer when multidrug resistance has occurred by administration of the derivatives and salts of this invention is also provided. Salts of anthracycline cations with their analogous glutathionyl anthracycline conjugate anions will be particularly useful in cases of multiple drug resistance.

The invention also provides a method of synthesizing the C-7 glutathionyl derivatives of anthracyclines.

DETAILED DESCRIPTION OF THE INVENTION

The process for the synthesis of the glutathionyl derivatives of this invention consists of the treatment of the anthracycline, under anaerobic conditions, with glutathione, at pH close to neutrality. The reaction is a reductive activation process, which is not a simple nucleophilic displacement, which occurs due to preliminary reduction of the anthracycline through the formation of the corresponding quinone methide which then alkylates the GSH. The anthracycline is reduced by glutathione itself or alternatively the reduction can be achieved by addition of other suitable reducing agents.

Scheme 1 illustrates a method of synthesis of the glutathionyl derivative of adriamycin. Sometimes, the tautomer of the quinone methide, i.e., the 7-deoxyaglycone (6) is obtained as a by-product.

In summary, formation of glutathione conjugates to aglycons of anthracyclines requires presence of a reducing agent, a pH in the range of 6–8 and an anaerobic medium. Glutathione itself can be the reducing agent or additional reducing agents can be added.

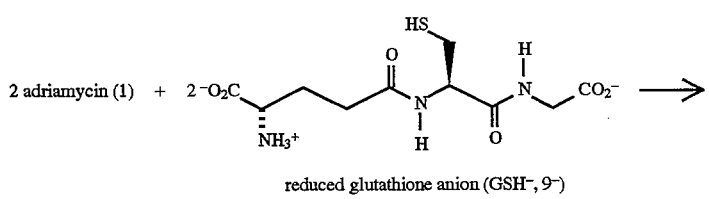

reduced glutathione anion (GSH⁻, 9⁻)

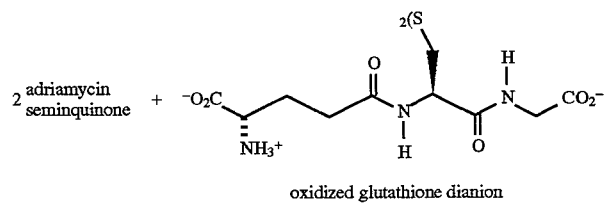

oxidized glutathione dianion

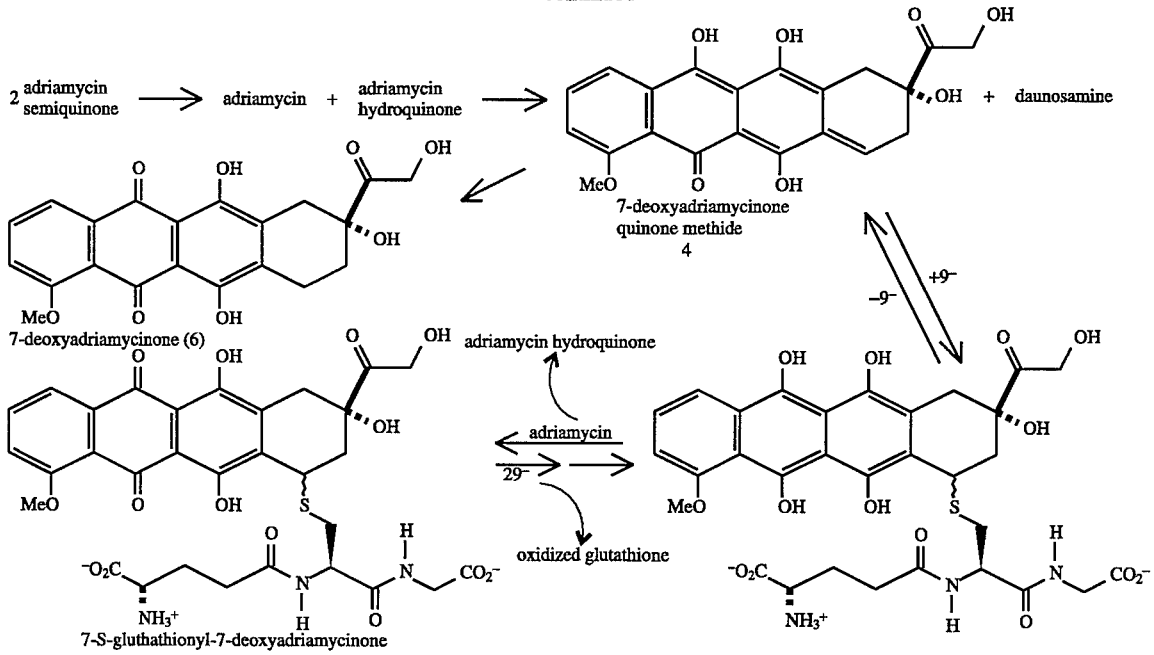

As stated above, the anthracycline derivatives and salts of this invention are useful antibiotic agents and anti-tumor agents having value in cancer chemotherapy and are of particular use in killing multidrug-resistant tumor cells.

Antibiotic pharmaceutical composition of this invention comprise a glutathione aglycon conjugate of an anthracycline in an amount effective for inhibiting the growth of a microorganism, and more specifically in an amount effective to produce a antimicrobial, bacteriostatic, or bacteriocidal effect. Preferred antibiotic compositions of this invention are useful in treatment of mammals.

An anti-tumor agent of this invention comprises a glutathione aglycon conjugate of an anthracycline in an amount effective for inhibiting tumor growth. Preferred anti-tumor agents of this invention are effective for treatment of tumors in mammals.

The glutathionyl anthracycline derivatives of this invention are of further use as a means for delivery of GSH into cells. Reductive activation of these new anthracyclines, which can occur in vivo, will release GSH. Released GSH can act as an inhibitor of the enzyme glutathione transferase which is thought to be responsible for some forms of multidrug resistance.

Examples:

Details of the preparation of glutathione anthracycline derivatives have been reported in Gaudiano, Get al. *J. Amer. Chem. Soc.* (1994) 116:6537. This report is incorporated in its entirely by reference herein.

Example 1:

The stereoisomers 7 I and 7 II obtained from adriamycin were synthesized as follows:

Adriamycin hydrochloride (40 mg), GSH (S) (0.42 g) and 0.25 g of Tris was dissolved in 17 ml of deuterowater $D_2O$, deareated with nitrogen. The solution was stirred under inert atmosphere and ambient temperature for 5 hours. The red precipitate obtained was collected, washed with water and dried. Yield: 39 mg (82%). The precipitate was purified by recrystallization from methanol. The purified precipitate was found to be the salt of ADRIGLU II with adriamycin (13).

Reverse phase HPLC of the recrystallized material (using Hewlett Packard 5 m C18 microbore 100 mm×2.1 mm column, 60:40 methanol/pH 4 formate buffer at 0.3 ml/min, monitoring at 480 nm) gave only two peaks of equal area at 1.8' and 7.0' which, corresponded to ADRIGLU II (7 II) and adriamycin (1) respectively.

The glutathione conjugate ADRIGLU II was separated from adriamycin by extraction of the latter with chloroform from a pH 10 aqueous solution of the salt. The mother liquors from which the precipitated salt had been separated, when analyzed by HPLC gave peaks corresponding to ADRIGLU II (7 II), adriamycin (1), traces of the 7-deoxyaglycone (6) at 7.8; and a peak at 1.5', corresponding to ADRIGLU I (7 I). The mass spectrum of ADRIGLU I showed the same molecular ion and fragmentation peaks as ADRIGLU II (7 II). The compound was separated from the mixture with no decomposition, by preparative HPLC. Its UV spectrum was identical to that of ADRIGLU II.

The same ADRIGLU I and II were obtained by reduction of adriamycin, in the presence of GSH, by sodium dithionite or the radical dimer DHM-3 (10a) in $D_2O$ or in water, in the absence of air, or in methanol using the radical dimer TM-3 (10b) as reducing agent.

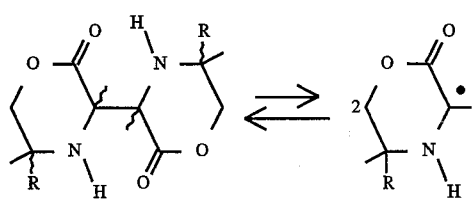

10a R = CH₂OH, DHM-3 dimer
10b R = CH₃, TM-3 dimer

R = CH₂OH, DHM-3
R = CH₃, TM-3

In a similar way quantitative yields of the corresponding glutathione derivatives DAUNOGLU I and II (8 I and II) from daunomycin were obtained in a 1:1 ratio. They showed mass spectra analogous to those from 7 I and 7 II.

Further, in a similar way, quantitative yields of the corresponding glutathione derivatives MENOGLU I and II (9) were obtained from menogaril. They both gave mass spectra perfectly analogous to those obtained from the corresponding derivatives of adriamycin and daunomycin.

Thus, the above-described process represents a general method for the synthesis, in high yields, of the glutathione conjugates of anthracyclines.

Those of ordinary skill in the art will appreciate that variations or modifications in reagents, reaction conditions, and techniques, other than those specifically described herein, are readily available to those in the art, can be applied to achieve the objects and goals of this invention and are thus encompassed by the spirit and scope of this invention.

We claim:

1. A compound which is a glutathione aglycon conjugate of an anthracycline or a semi-synthetic anthracycline or pharmaceutically acceptable salts of the anion thereof wherein the anthracycline or semi-synthetic anthracycline is substituted at the C-7 position with the glutathione.

2. The compound of claim 1 represented by the formula:

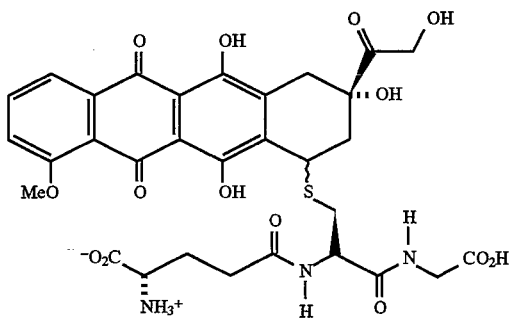

or pharmaceutically acceptable salts of the anion thereof.

3. The compound of claim 1 represented by the formula:

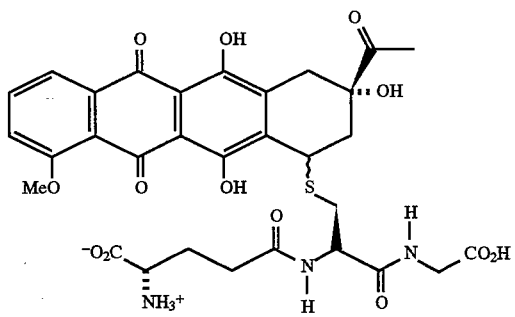

or pharmaceutically acceptable salts of the anion thereof.

4. The compound of formula 1 represented by the formula:

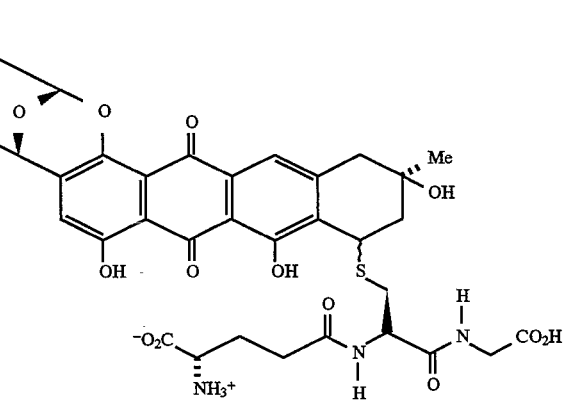

or pharmaceutically acceptable salts of the anion thereof.

5. An antibiotic pharmaceutical composition which comprises a glutathione aglycon conjugate of an anthracycline of claim 1 in an amount effective for inhibiting the growth of a microorganism and a pharmaceutically acceptable carrier.

6. An anti-tumor agent which is a composition which comprises a glutathione aglycon conjugate of an anthracycline of claim 1 in an amount effective for inhibiting tumor growth.

7. A salt that comprises a glutathione aglycon conjugate anion of an anthracycline or semi-synthetic anthracycline in combination with an anthracycline or semi-synthetic anthracycline cation, wherein the anthracycline or semi-synthetic anthracycline conjugate anion is substituted at the C-7 position with the glutathione.

8. The salt of claim 7 wherein the anthracycline is selected from the group consisting of adriamycin, daunomycin or menogaril.

9. The compound of claim 1 which is a glutathione aglycon conjugate of an anthracycline or pharmaceutically acceptable salts of the anion thereof.

10. The salt of claim 7 which comprises a glutathione aglycon anthracycline cation.

11. The salt of claim 7 which is the salt of the adriamycin cation with the glutathionyl adriamycin conjugate anion.

* * * * *

UNITED STATES PATENT AND TRADEMARK OFFICE
CERTIFICATE OF CORRECTION

PATENT NO. : 5,646,177

DATED : July 8, 1997

INVENTOR(S) : Koch et al.

Page 1 of 3

It is certified that error appears in the above-identified patent and that said Letters Patent is hereby corrected as shown below:

In column 1, lines 23-36, please replace the structure of adriamycin (1) and daunomycin (2) with the following structure:

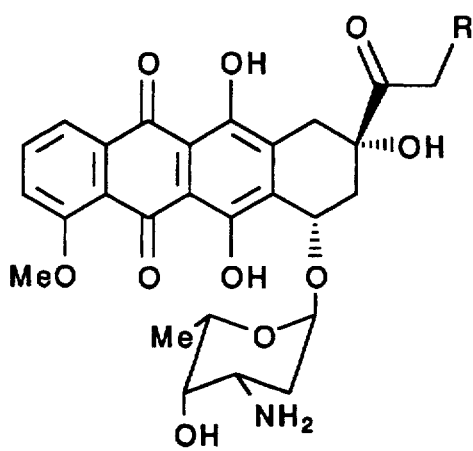

UNITED STATES PATENT AND TRADEMARK OFFICE
CERTIFICATE OF CORRECTION

PATENT NO. : 5,646,177
DATED : July 8, 1997
INVENTOR(S) : Koch et al.

It is certified that error appears in the above-identified patent and that said Letters Patent is hereby corrected as shown below:

In column 3, line 15, please replace the structure of 7I and 7II with the following structure:

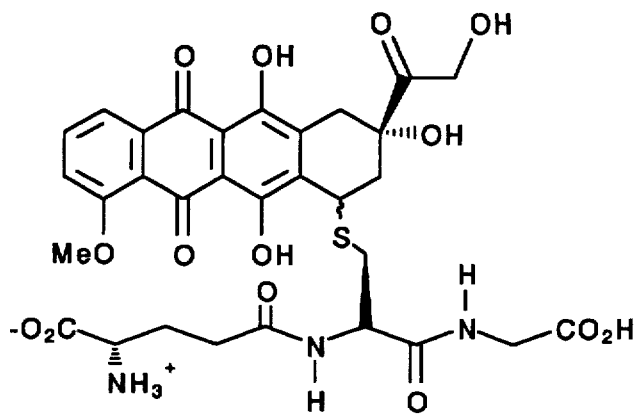

Below the compound located in columns 3 and 4 at about line 45, please insert --7-S-glutathionyl-7-deoxynogarol--.

UNITED STATES PATENT AND TRADEMARK OFFICE
CERTIFICATE OF CORRECTION

PATENT NO. : 5,646,177

DATED : July 8, 1997

INVENTOR(S) : Koch et al.

It is certified that error appears in the above-identified patent and that said Letters Patent is hereby corrected as shown below:

Please replace the conjugate anion structure at the top of column 5 with the following structure:

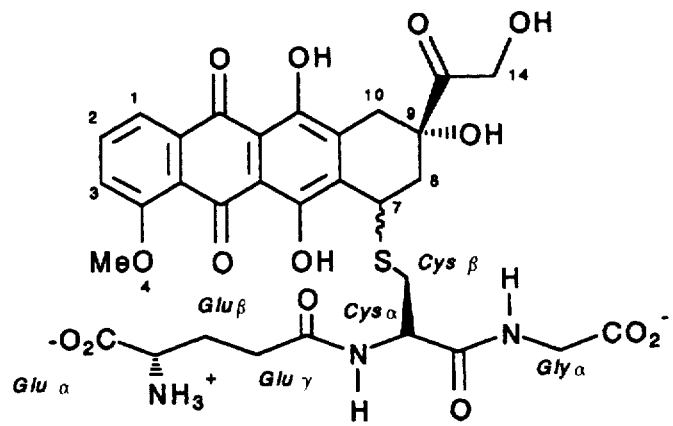

Signed and Sealed this

Thirtieth Day of December, 1997

Attest:

BRUCE LEHMAN

Attesting Officer

Commissioner of Patents and Trademarks